US00PP30460P3

(12) United States Plant Patent
Klemm et al.

(10) Patent No.: US PP30,460 P3
(45) Date of Patent: Apr. 30, 2019

(54) ***PELARGONIUM* PLANT NAMED 'KLEPZ17154'**

(50) Latin Name: *Pelargonium zonale*
Varietal Denomination: KLEPZ17154

(71) Applicant: Klemm+Sohn GmbH & Co. KG, Stuttgart (DE)

(72) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 15/932,937

(22) Filed: May 23, 2018

(65) Prior Publication Data

US 2018/0343781 P1 Nov. 29, 2018

(30) Foreign Application Priority Data

May 24, 2017 (CH) ..... PBR 17-3143

(51) Int. Cl.
*A01H 5/02* (2018.01)
*A01H 6/42* (2018.01)

(52) U.S. Cl.
USPC ..... Plt./329
CPC ..... *A01H 6/425* (2018.05)

(58) Field of Classification Search
USPC ..... Plt./263.1, 324, 325, 329
See application file for complete search history.

*Primary Examiner* — Susan McCormick Ewoldt
*Assistant Examiner* — Karen M Redden
(74) *Attorney, Agent, or Firm* — Bethany R. Roahrig; Cochran Freund & Young LLC

(57) ABSTRACT

A new *Pelargonium* plant particularly distinguished by red flowers with red-purple shading, medium leaf zonation, and an upright growth habit, is disclosed.

1 Drawing Sheet

Genus and species: *Pelargonium zonale*.
Variety denomination: 'KLEPZ17154'.

CROSS REFERENCE TO RELATED APPLICATIONS

The present application claims priority to Switzerland Plant Variety Protection Application No. 17-3143, as filed on May 24, 2017, the entire contents are herein incorporated by reference for all the application teaches and discloses. A European Community Plant Variety Protection Application was filed on May 31, 2017, Application No. 2017/1447.

BACKGROUND OF THE NEW PLANT

The present invention comprises a new and distinct variety of *Pelargonium*, botanically known as *Pelargonium zonale* and hereinafter referred to by the variety name 'KLEPZ17154'. 'KLEPZ17154' originated from a hand pollination in July 2012 in Stuttgart, Germany between the proprietary female *Pelargonium* variety 'KLEPZ12322' (unpatented) and the male *Pelargonium* variety ATLANTIC 'Royal White' (unpatented).

Seeds from the cross-combination were obtained and sown and plants were grown for evaluation. A single plant was selected in June 2013 and subsequently named 'KLEPZ17154'. In September 2013 'KLEPZ17154' was first vegetatively propagated in Stuttgart, Germany by vegetative cuttings from branches. 'KLEPZ17154' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. Red-purple flowers;
2. Medium leaf zonation; and
3. An upright growth habit.

DESCRIPTION OF THE PHOTOGRAPH

This new *Pelargonium* plant is illustrated by the accompanying photograph which shows an overall view of the plant. The photograph is of an approximately 10 week old plant grown in Stuttgart, Germany under greenhouse conditions in June 2016.

The colors shown are as true as can be reasonably obtained by conventional photographic procedures.

DESCRIPTION OF THE NEW VARIETY

The following detailed descriptions set forth the distinctive characteristics of 'KLEPZ17154'. The data which define these characteristics were collected from asexual reproductions carried out in Stuttgart, Germany. Data was collected on plants grown three months after planting in Stuttgart, Germany under a glass covered greenhouse in April 2018. Color references are to The R.H.S. Colour Chart of The Royal Horticultural Society of London (R.H.S.), 5$^{th}$ edition (2007).

Classification:
*Family.*—Geraniaceae.
*Botanical.*—*Pelargonium zonale.*
*Common.*—*Pelargonium.*
*Designation.*—'KLEPZ17154'.

Parentage:
*Female.*—'KLEPZ12322' (unpatented).
*Male.*—ATLANTIC 'Royal White' (unpatented).

Plant:
*Form.*—Bushy and round.
*Habit.*—Upright.
*Height.*—14.0 cm to 14.5 cm.
*Spread.*—16.0 cm to 20.5 cm.
*Natural flowering season.*—April to October.
*Propagation type.*—Vegetative cuttings.
*Time to produce a finished flowering plant.*—3 months.
*Time to initiate and develop roots.*—4 weeks.
*Root description.*—White and fine.

Stems:
*Quantity of stems per plant.*—3.
*Color.*—RHS 144A.
*Surface texture.*—Sparsely pubescent.
*Stem form.*—Round.
*Diameter.*—0.5 cm to 0.8 cm.
*Length.*—3.5 cm to 9.0 cm.
*Internode length.*—1.3 cm to 2.5 cm.
*Anthocyanin.*—Absent.

Leaves:
*Arrangement.*—Alternate.
*Shape.*—Reniform.
*Apex.*—Round.
*Base.*—Slightly open.
*Margin.*—Crenate.
*Texture* (*both surfaces*).—Sparsely pubescent.
*Length.*—3.0 cm to 4.4 cm.
*Width.*—5.5 cm to 6.7 cm.
*Color.*—Upper surface: RHS N137A. Lower surface: RHS 137C.
*Zonation.*—Present, color RHS N187A.
*Zone conspicuousness.*—Medium.
*Zone position.*—Middle.
*Zone width.*—0.6 cm to 1.0 cm.
*Petiole.*—Length: 3.5 cm to 4.0 cm. Diameter: 0.2 cm to 0.3 cm. Color: RHS 143A. Strength: Moderate.
*Venation pattern.*—Palmate.
*Venation color.*—Upper surface: RHS 143A. Lower surface: RHS 144A.

Inflorescence:
*Lastingness of flowers on the plant.*—6 to 8 days.
*Umbels.*—Quantity of umbels per plant: 4 to 6. Length: 6.0 cm. Diameter: 8.5 cm to 10 cm.
*Individual florets of the umbel.*—Quantity of florets per umbel: 12. Depth: 1.5 cm. Diameter: 4.0 cm to 5.0 cm.
*Fragrance.*—Absent.

Flower buds:
*Cluster shape.*—Round.
*Cluster size.*—Length: 1.1 cm to 1.5 cm. Width: 1.2 cm to 2.0 cm.
*Surface texture.*—Sparsely pubescent.
*Bud.*—Height: 0.6 cm. Width: 0.6 cm. Shape: Round. Apex: Acute. Base: Obtuse. Margin: Entire. Color: RHS 144A.

Petals:
*Quantity per flower.*—7 to 9.
*Shape.*—Spatulate.
*Apex.*—Round.
*Base.*—Obtuse.
*Margin.*—Entire.
*Length.*—2.5 cm.
*Width.*—2.1 cm to 2.5 cm.
*Texture* (*both surfaces*).—Smooth.
*Color of lobes.*—Upper and lower lobes: Upper surface: RHS 45B with shading colored RHS N57A. Lower surface: RHS 45C.

Petaloids:
*Quantity per flower.*—3 to 4.
*Shape.*—Mixed.
*Apex.*—Mixed.
*Base.*—Obtuse.
*Margin.*—Entire.
*Length.*—1.0 cm to 2.0 cm.
*Width.*—0.4 cm to 1.3 cm.
*Texture* (*both surfaces*).—Smooth.
*Color.*—Upper surface: RHS 45B with shading colored RHS N57A. Lower surface: RHS 45C.

Sepals:
*Number per flower.*—5.
*Shape.*—Elliptic.
*Apex.*—Acute.
*Base.*—Obtuse.
*Margin.*—Entire.
*Surface texture.*—Upper surface: Smooth. Lower surface: Sparsely pubescent.
*Color.*—Upper surface: RHS 144A from middle to tip; RHS 181A from base to middle. Lower surface: RHS 143A from middle to tip; RHS 182A from base to middle.
*Length.*—1.1 cm.
*Width.*—0.4 cm.

Pedicel:
*Length.*—2.5 cm.
*Diameter.*—0.2 cm.
*Color.*—RHS 178A.
*Surface texture.*—Sparsely pubescent.
*Strength.*—Moderate.

Peduncle:
*Length.*—7.0 cm to 8.0 cm.
*Diameter.*—0.4 cm.
*Color.*—RHS 143A.
*Surface texture.*—Sparsely pubescent.
*Strength.*—Moderate.

Reproductive organs:
*Stamens.*—Quantity of stamens per flower: 3 to 6. Anther length: 0.3 cm. Filament length: 0.8 cm. Filament color: RHS 96A at base, RHS N57A at tips. Pollen amount: Moderate. Pollen color: RHS 178D.
*Pistils.*—Number: 1. Stigma color: RHS 181A. Style length: 0.2 cm. Style color: RHS 181A. Ovary arrangement: Central. Ovary color: RHS 178A; RHS 143C at base. Ovary diameter: 0.2 cm. Ovary length: 0.6 cm.

Fruit and seed set: None observed.

Disease and pest/insect resistance: None observed.

COMPARISON WITH PARENTAL LINES AND KNOWN VARIETY

'KLEPZ17154' is distinguished from its parents as described in Table 1:

TABLE 1

| Comparison with Parental Lines | | | |
|---|---|---|---|
| Characteristic | 'KLEPZ17154' | Female 'KLEPZ12322' | Male ATLANTIC 'Royal White' |
| Leaf zonation | Medium | Very weak | Very strong |
| Flower color | Red with red-purple shading | Purple, pink, and red | White |

'KLEPZ17154' can be compared to the commercial variety 'Sil Magnus'. (unpatented). Differences between the two varieties are described in Table 2:

TABLE 2

| Comparison with Similar Variety | | |
|---|---|---|
| Characteristic | 'KLEPZ17154' | Commercial line 'Sil Magnus' |
| Leaf zonation | Medium | Very weak |
| Flower color | Red with red-purple shading | Purple, pink, and red |

We claim:

1. A new and distinct variety of *Pelargonium* plant named 'KLEPZ17154' as illustrated and described herein.

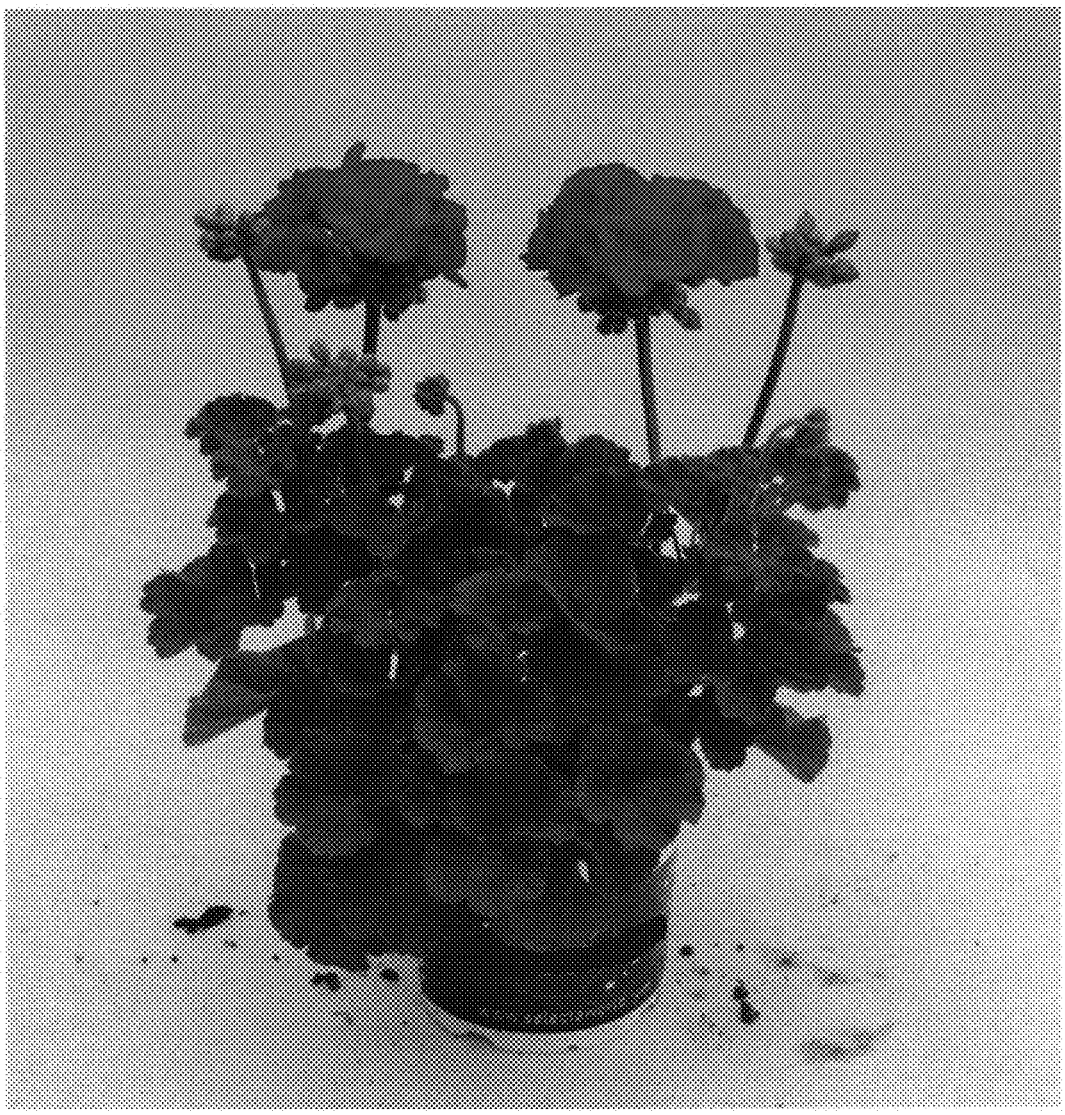

* * * * *